(12) United States Patent
Rauchenzauner et al.

(10) Patent No.: US 8,137,102 B2
(45) Date of Patent: Mar. 20, 2012

(54) FLUID-OPERATED MEDICAL OR DENTAL HANDHELD ELEMENT

(75) Inventors: Stephan Rauchenzauner, Signature Park (SG); Karl Schmiedlechner, Ostermiething (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 256 days.

(21) Appl. No.: 12/106,997

(22) Filed: Apr. 21, 2008

(65) Prior Publication Data

US 2008/0261172 A1 Oct. 23, 2008

(30) Foreign Application Priority Data

Apr. 20, 2007 (EP) ..................................... 07008056
Apr. 9, 2008 (EP) ..................................... 08007019

(51) Int. Cl.
*A61C 1/05* (2006.01)

(52) U.S. Cl. ... 433/132; 433/114; 433/133; 310/40 MM

(58) Field of Classification Search .......... 433/131–133, 433/82, 84, 114, 86, 103, 120; 310/40 MM, 310/113, 154.01, 105, 50, 47, 49.29; 290/54; 362/119; 464/18, 30, 182, 901; 173/216–218, 173/222, 164; 315/55
See application file for complete search history.

(56) References Cited

U.S. PATENT DOCUMENTS

| | | | |
|---|---|---|---|
| 4,568,642 A * | 2/1986 | DeForrest et al. ............. | 433/132 |
| 4,642,738 A * | 2/1987 | Meller ........................... | 362/119 |
| 4,725,232 A | 2/1988 | Hatakeyama | |
| 5,267,129 A * | 11/1993 | Anderson ........................ | 362/96 |
| 5,457,611 A * | 10/1995 | Verderber ...................... | 362/572 |
| 5,507,642 A * | 4/1996 | Wohlgemuth ................. | 433/132 |
| 5,800,172 A | 9/1998 | Goldenberg | |
| RE36,917 E * | 10/2000 | Leininger ....................... | 290/54 |
| 6,186,784 B1 * | 2/2001 | Bailey ............................ | 433/126 |
| 6,270,342 B1 * | 8/2001 | Neuberger et al. ............. | 433/29 |
| 6,906,466 B2 * | 6/2005 | Feng .............................. | 315/55 |

(Continued)

FOREIGN PATENT DOCUMENTS

GB 1 371 525 10/1974
(Continued)

OTHER PUBLICATIONS

European Search Report for EP 07 00 8056 (Mailed Aug. 8, 2007).
(Continued)

*Primary Examiner* — Cris L Rodriguez
*Assistant Examiner* — Edward Moran
(74) *Attorney, Agent, or Firm* — Klarquist Sparkman, LLP

(57) ABSTRACT

A fluid-operated medical or dental handheld element is disclosed, having a connecting device for connecting the handheld element to a fluid source so that a first impeller can be induced to rotate by a fluid stream to cause a tool to execute a driving motion, a fluid conducting device arranged between the connecting device and the first impeller for conveying a fluid stream away from or toward the first impeller, and a generator for generating electric power. The generator includes a second rotatable impeller that can be driven by at least a substream of the fluid stream conveyable in the first fluid conducting device. One result is more constant generation and output of power by the generator independent of the rotational speed of the first impeller, thereby insuring a more constant power supply to a power consuming device connected to the generator.

39 Claims, 5 Drawing Sheets

U.S. PATENT DOCUMENTS 7,095,142 B2 * 8/2006 Leininger ..................... 310/47

FOREIGN PATENT DOCUMENTS

| JP | 60-203247 | | 10/1985 |
|---|---|---|---|
| JP | 60-253437 | | 12/1985 |
| JP | 61-8042 | * | 1/1986 |
| JP | 2004-248991 | | 9/2004 |
| WO | 01/12095 | | 2/2001 |

OTHER PUBLICATIONS

European Search Report for EP 08007019 (mailed Aug. 14, 2008).

* cited by examiner

FLUID-OPERATED MEDICAL OR DENTAL HANDHELD ELEMENT

CROSS REFERENCE TO RELATED APPLICATION

The present application claims priority from pending European Patent Application No. 07008056.9, filed Apr. 20, 2007, and European Patent Application No. 08007019.6, filed Apr. 9, 2008, both of which are incorporated herein by reference.

BACKGROUND

1. Field

This application relates to a fluid-operated medical or dental handheld element with a generator for generating electric power.

2. Description of Prior Art

U.S. Pat. No. 5,800,172 discloses a turbine handpiece in which the impeller, which is operated by compressed air and induces rotation of the tool, is also used as part of an electromechanical transformer which generates electric current for a light source provided in the head of the handpiece.

One disadvantage of this turbine handpiece is that the rotational speed of the impeller and thus the power generated by the generator fluctuate constantly during operation. Such fluctuations are induced by different loads on the turbine handpiece, e.g., when the user places the tool connected to the impeller on the object to be processed or when the user exerts pressure on the object to be processed via the handpiece. The variable generation and output of power by the generator also lead to constant fluctuations in the light emitted by the light source and in particular lead to extremely weak illumination of the preparation site at low rotational speeds.

Therefore, it would be advantageous to create a fluid-operated medical, in particular dental, handheld element which does not have the disadvantages mentioned above and in particular has a uniform light output.

SUMMARY

According to an embodiment, the fluid-operated medical or dental handheld element comprises a connection device for connecting the handheld element to a fluid source and a fluid conducting device arranged to supply fluid from the connecting device to a first impeller to induce its rotation and thereby cause a tool connected to the first impeller to execute a working motion. The handheld element is also provided with a generator for generating electric power, such that the generator comprises a second impeller that can be induced to rotate and can be driven with at least a substream of the fluid stream conveyable in the first fluid conducting device.

Due to this design, a substantially constant generation and output of power by the generator are achieved, thus ensuring a constant power supply to a consumer (or power consuming device) electrically connected to the generator. Preferably a radiation source, in particular a light source comprising at least one light-emitting diode, is provided as the consumer. As soon as the handheld element is connected to a fluid source, the two impellers are driven by the fluid such that the reduction in the rotational speed of the first impeller driving the tool has no effect on the rotational speed of the second, or generator, impeller. Even if the first impeller and the tool connected to it are brought to a standstill by the action of external forces, the generation of power by the generator and in particular the output of radiation by the radiation source continue.

The drive of the second impeller with at least a substream of the fluid stream conveyable in the fluid conveying device also yields a considerable advantage in the design of the handheld element, in particular a simplification of the design of the connecting device and the supply system connected to the connecting device, e.g., a supply tube which connects the handheld element to the fluid source. The connecting device may be designed in a known way as a plug connection, a screw connection, a clamp connection or a twist connection, for example, such that regardless of the type of connection, the design and creation of the connecting device should be as simple as possible. This is achieved by driving the second impeller with at least a substream of the fluid stream conveyable in the first fluid conducting device, in which case only one fluid conducting device (e.g., a passageway or a fluid line) need be provided for the drive of the two impellers in the connecting device.

The generators are understood to be in particular electrodynamic or electromechanical transformers that are used to generate electric power. For driving these generators, a fluid or a fluid mixture is used, e.g., a liquid or a gas, in particular water or compressed air. The second impeller may have different designs or embodiments, e.g., it may be designed as a turbine impeller, like the rotors in turbine handheld devices operated with compressed air or as a rotating piston air engine or a vane motor such as those used in medical air motors, for example.

The term handheld element as used herein includes straight handpieces, curved handpieces, which are often referred to as contra-angle handpieces in the dental field, as well as parts of handpieces and/or handpiece assemblies. Such parts include, for example, various handle sections for a handpiece, various head sections for different tools, etc. The parts of the handpiece may also include intermediate pieces, such as coupling devices, adapters or independent sleeve sections, for example.

In one embodiment, the generator impeller and the first impeller are arranged in series. The fluid flows first through the generator and the generator impeller, and is then conveyed to the first impeller, which is situated downstream. In this embodiment the design is especially simple because only a single fluid conducting device is needed to conduct the fluid and to supply the two rotors with fluid.

In an alternative embodiment, the generator impeller and the first impeller are arranged in parallel. In the alternative embodiment, a first fluid conducting device connects the connecting device and the fluid source to the first impeller, and a second fluid conducting device connects the connecting device and the fluid source to the generator, such that the second fluid conducting device is connected to or branches off from the first fluid conducting device. One advantage of this arrangement is reducing contamination of the generator due to soiling and particles that are drawn into the first fluid conducting device during operation of the first impeller. There is thus also the possibility of supplying both rotors with fluid at approximately the same fluid pressure and approximately the same fluid flow rate, so that the same types of rotors, e.g., a Pelton wheel, may be used for the tool drive as well as for the generator.

In another embodiment, the generator is accommodated at least partially in one of the two fluid conducting devices. In other embodiments, preferably the entire generator is accommodated in the fluid conducting device. This achieves in an advantageous manner the result that the generator is at least partially or entirely surrounded by fluid flow around it and/or through it and is thus thoroughly cooled. To be able to accommodate the generator, the fluid conducting device has an enlarged diameter in this area, thus forming a receptacle, a widened area, a cavity or a chamber into which the generator can be inserted.

The fluid conducting device may comprise any form of suitable passageway, and may also comprise other components, e.g., bores, channels or sleeves in addition to one or more tubular, straight or curved line sections. In particular in the area having the enlarged diameter, the fluid conducting device is composed of several components which are designed in the form of a sleeve or funnel. The term fluid conducting device is thus also to be understood to include the fluid-tight connection of several components of the type mentioned above. To eliminate pressure fluctuations in the drive fluid, a regulating valve is preferably provided in the fluid conducting device.

In one embodiment, the generator is at least partially surrounded by an outer shell which forms a cartridge and can be inserted detachably into the fluid conducting device. The generator module formed by the cartridge preferably comprises the rotor with the rotor shaft on which the second impeller and the rotor magnet are attached, the stator, the bearings for rotatable mounting of the rotor shaft, electric contacts for deriving the electric current generated by the generator and the outer shell formed by one or more sleeves. One or more conducting elements for guiding the fluid stream and for directed output of the fluid stream onto the second impeller and one or more electric or electronic components, e.g., a transformer or a rectifier, preferably mounted on a circuit board, are especially preferably also included in the cartridge. The advantage of this embodiment lies in the easy replaceability of such a generator module, e.g., when there is a defect.

If the generator is surrounded with such an outer shell, one or more passages such as recesses, openings or bores must be provided so that the drive fluid can be carried to the generator rotor, in particular through the outer shell to the generator rotor arranged in the interior of the generator and/or so that the drive fluid can be carried away from the generator rotor, in particular toward the outside through the outer shell of the generator. The outer shell of the generator is preferably arranged at a distance from the fluid conducting device at least in a partial section so that a gap is formed between the inside wall of the fluid conducting device and the outer shell of the generator, serving as a fluid channel for conducting the fluid stream. This fluid channel is connected or adjacent to the at least one passage in the outer shell of the generator so that the fluid stream flows to the generator rotor and/or away from the generator rotor.

The at least one passage is especially preferably provided in proximity to the generator rotor so that the fluid stream flows essentially only in the area of the generator rotor in the interior of the generator cartridge, whereas the section of the generator cartridge in which the stator, the rotor magnet and the electric and/or electronic component are arranged does not have fluid flowing through it but instead fluid flows only around it on the outside. The passage is arranged in particular in the outer shell of the generator so that the fluid stream can be conducted through the outer shell of the generator. The advantage of this fluid guidance lies in both effective cooling and dissipation of heat because the entire generator has fluid flowing around it and/or through it but also lies in a reduction in the risk of soiling of the stator, the rotor magnet and the electric and/or electronic components due to dust particles and precipitants present in the fluid and in particular due to lubricant for lubricating moving parts in the handheld element.

In an embodiment, the handheld element has an elongated shape with a first end and a second end such that the first fluid line and/or the second fluid line extend essentially in an axial direction between the two ends of the handheld element over at least a section so that the fluid stream can be conveyed axially at least in this section and at least one guide element is provided for tangential and/or radial deflection of the fluid stream onto the second impeller. In another embodiment, the handheld element has an elongated shape with a first end and a second end, with the axis of rotation of the generator rotor extending essentially axially between these two ends, and such that the generator rotor is arranged in the handheld element in such a way that the fluid stream can flow toward it tangentially and/or radially. In both embodiments, the generator and/or the generator cartridge is/are thus designed as an elongated, preferably cylindrical unit which has a large outside surface area over which a cooling fluid can be passed so as to achieve effective dissipation of heat.

Owing to the axial fluid flow around the elongated generator design, it is necessary in particular to provide one or more guide elements which carry the fluid and guide it to the generator rotor in such a way as to provide optimized oncoming flow so that the generator rotor can be driven with a high efficiency. The guide element has different geometric elements for this purpose, e.g., grooves, channels, vanes or blades.

The generator is preferably provided with a one-piece rotatable generator shaft on which the second impeller and the rotor are arranged, and wherein there is provided at least one bearing for supporting the generator shaft which does not require an external lubricant supply in the assembled state, i.e., lubricant need not be introduced into the bearing from outside of the handheld element, the at least one bearing may be in particular a friction bearing, a hydro bearing, an air bearing or at least a roller bearing having a ceramic material. The advantage of using this bearing consists of the fact that the danger of failure of the generator due to sticking of the rotor and the generator shaft is definitely reduced and/or eliminated.

Many handheld elements contain moving parts that require repeated lubrication with a lubricant for long-term operation. This is usually accomplished by a non-targeted introduction of lubricant into the handheld element, e.g., into the fluid conducting device, and by conveying the lubricant through the handheld element and past components arranged in the handheld element or through and past the components up to the actual component to be lubricated. As a result of this procedure, lubricant adheres not only to the component that requires lubrication but also to many other components, e.g., on and in the generator.

When using unsuitable lubricants or after repeated sterilization, there may be changes in the lubricant, in particular changes in viscosity and solidification of the lubricant. In experiments, the present applicant has found that these changes in the lubricant may in many cases result in complete blockage of the generator, in particular the generator shaft, due to sticking of the bearings which provide the bearing support of the generator shaft. The blockage of the generator shaft was so tight that even conveyance of fluid through the generator was unable to loosen the blocked shaft, so the entire generator and consequently also the handheld element could no longer be used. Surprisingly, in particular friction bearings which do not themselves require any external supply of lubricant and which, because of their compact design, offer only very minor adhesive surfaces on which the lubricant—that is supplied for the other components in the handheld element—can be deposited and can solidify have proven to be far less susceptible to this type of blockage and jamming in comparison with all other types of bearings tested. The use of roller bearings with ceramic components, e.g., ceramic bearing races and/or ceramic roller bodies or other roller bearings that can be operated without lubricant also reduces the risk of blockage of the generator shaft due to changes in the lubricant.

For axial bearing support of the generator shaft, in one embodiment a spot bearing is used which is arranged downstream from the second impeller. The generator shaft has a rounded or pointed end which has a bearing body with a rounded or pointed surface, e.g., a sphere, a hemisphere, a cone or a truncated cone. Due to the arrangement of the spot bearing downstream from the second impeller, an extremely effective bearing support for the generator shaft is achieved in an advantageous manner without requiring any additional fixation or prestressing of the generator shaft to do so because the fluid stream presses the impeller and the generator shaft connected to it automatically in the direction of the spot bearing. The spot bearing in particular in combination with the friction bearing thus allows a simple, reliable and inexpensive means of providing bearing support for the generator shaft. The spot bearing also results in minimized friction between the generator shaft and the bearing body so the loss of power by the generator is minimized.

In one embodiment, the handheld element comprises an electric line for connecting the generator to a consumer, such that the electric line passes through the wall of the first and/or second fluid conducting device and a sealing device is provided for sealing the passage of the electric line through the first and/or second fluid conducting device(s). In particular when the generator is accommodated in the fluid conducting device, it is advantageous from the design standpoint to arrange the electric line at least partially in the fluid conducting device. If the consumer is arranged outside of the fluid conducting device, then the electric conductor passes through the side wall of the fluid line, such that to seal off and prevent any loss or escape of fluid, a sealing device is provided for sealing the passage of the electric conductor through the fluid conducting device. The sealing device is preferably arranged on a carrier element on which electric contact elements are provided for connecting the electric line to the generator; the carrier element is especially preferably designed as part of the fluid conducting device for conducting the fluid stream to the generator.

In an especially preferred embodiment, the generator of the handheld element supplies electric power to a lighting device, wherein the lighting device has a hermetically encapsulated interior space in which at least one optical semiconductor element is arranged. Due to this design, the entire handheld element together with the generator and the lighting device can be sterilized or exposed to aggressive cleaning agents or disinfectants. If there is nevertheless a failure of the lighting device due to impacts or in particular due to mechanical destruction of the surface due to scratching, the lighting device is also designed to be detachably arranged in the handheld element so that it is replaceable by a new intact lighting device.

The generator is preferably installed eccentrically in the handheld element so that there is enough space to be able to guide additional components accommodated in the handheld element, in particular media lines, past the generator.

These and other embodiments will be explained in greater detail below on the basis of several preferred embodiments and with reference to the accompanying drawings, in which:

DETAILED DESCRIPTION

Figure 1:
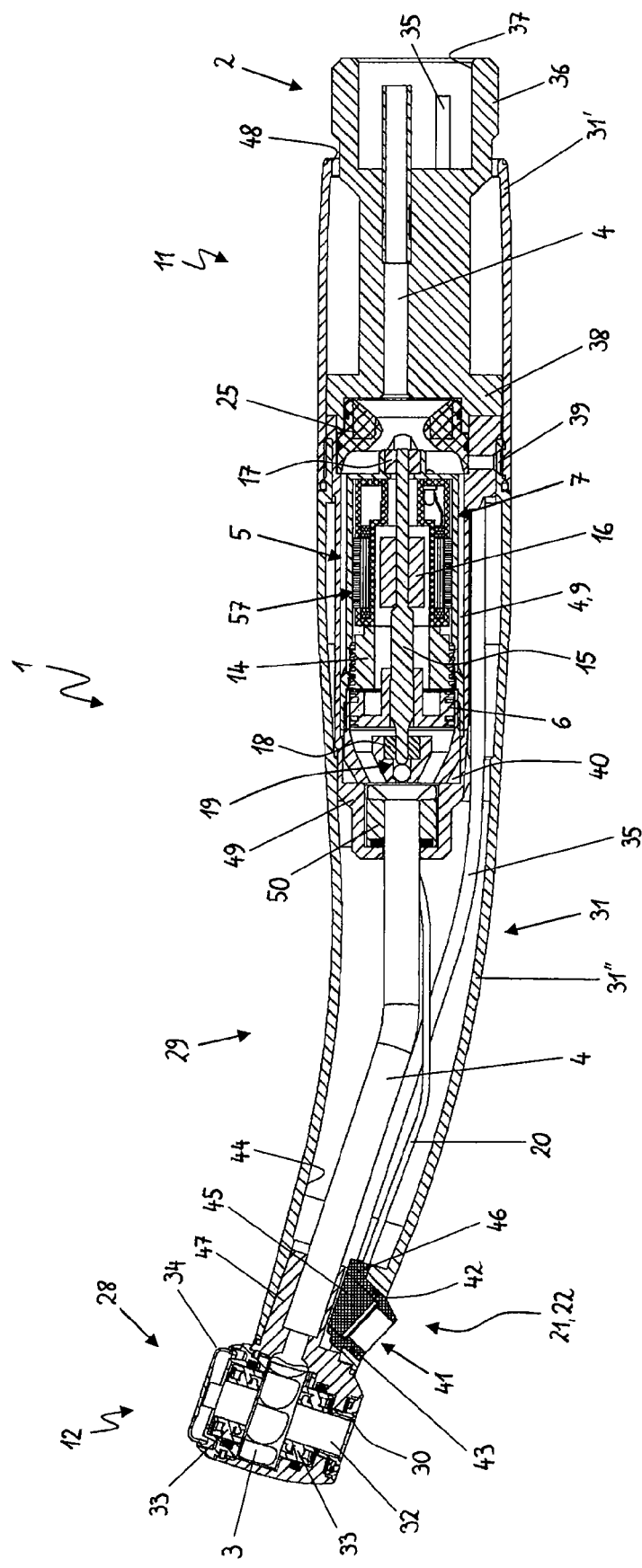
FIG. 1 shows an embodiment of a fluid-operated medical or dental handheld element with a generator, wherein the generator impeller and the impeller for driving the tool are supplied with a drive fluid through a common fluid conducting device.

The medical or dental medical handheld element 1 illustrated in FIG. 1 has a first end 11 and a second end 12. The second end 12 is designed as a head section 28 to which an elongated handle section 29 is detachably connected. The handheld element 1 is designed as a so-called contra-angle handpiece in which the handle section 29 consists of two sections arranged at angles to one another and in which the tool opening 30 is arranged at the side of the head section 28, so that a treatment tool can be inserted into the head section 28 transversely the handle section 29. An outer sleeve 31 in one or more parts surrounds the handle section 29 and the head section 28. The handheld element may of course also have other outer shapes, in particular a straight shape or a pistol shape.

In the front area or head section 28 of the handle element 1 there is a tool receptacle 32 that is accessible through the tool opening 30 in a known manner. The tool receptacle 32 is accommodated at least partially in a hollow shaft which is movably mounted, in particular through two ball bearings 33. By means of a drive fluid, e.g., compressed air, a first impeller 3 which is mounted on the hollow shaft, can be set in rotation jointly with the hollow shaft and the tool receptacle 32. A tool release mechanism 34 with a pushbutton facilitates the removal of a tool, e.g., a rotary drill, that can be inserted into the tool receptacle 32.

The first impeller 3 is designed as a free-jet or equal pressure turbine, i.e., the dynamic pressure applied in the fluid is used to drive the impeller 3 and is dissipated via the impeller 3 so that the dynamic pressure (flow pressure) of the drive fluid is higher upstream from the impeller 3 or before the encounter with the impeller 3 than downstream from the impeller 3. The driving of the impeller 3 therefore takes place by the kinetic energy contained in the drive fluid. As impeller 3 for example a Pelton impeller or an impeller similar to a Pelton impeller is used. Fluid is supplied to the first impeller 3 via a fluid conducting device 4 which extends from the connecting device 2 through the entire handheld element 1 up to the head section 28. At the end of the fluid conducting device 4 near the head, the fluid emerges from the conducting device 4 as a free stream and strikes the first impeller 3. The first impeller 3 is accommodated in a chamber from which at least most of the fluid enters into a return line. The return line comprises either a separate line which again passes through the handheld element 1 or is formed by the outer sleeve 31 of the handheld element 1.

At the first end 11 of the handheld element 1, a connecting device 2 is provided for direct or indirect connection of the handheld element 1 to a control and/or supply device. The connecting device 2 may be designed in particular as a plug coupling, a screw connection, a clamp or rotary coupling or connection which is connectable to a supply tube in which one or more media lines are arranged. Multiple bores, channels or lines for transfer of media are provided in the connecting device 2, e.g., a water line 35 and a fluid or compressed air line 4. The water line 35 runs through the handheld element 1 up to the head section 28 where the water becomes mixed with compressed air and is discharged through openings on the head section 28.

The connecting device 2 is accommodated in a separate part 31' of the outer sleeve 31. The outer sleeve 31 is connected by a thread 39 to the outer sleeve part 31". The connecting device 2 has an elongated shape and is provided with a thread 36 on its end facing away from the head section 28 for connecting it to the supply tube and with a receptacle 37 for a coupling mating piece of the supply tube. On its end facing the head section 28 the connecting device 2 has a flange-like widened part 38 through which bores for screws pass through which the connecting device 2 is connected and attached to components in the outer sleeve part 31". Alternatively, the connecting device 2 is accommodated in the outer sleeve part 31' and is put under tension by the screw connection of the two outer sleeve parts 31', 31" in the handheld element 1.

The generator 5 for generating electric power is connected to the connecting device 2 and/or to the part of the fluid line 4 passing through the connecting device 2. The fluid flows first through the generator 5 and is then sent on to the first impeller 3 situated downstream, so the second (generator) impeller 6 and the first impeller 3 are thus arranged in series or one after the other. The fluid line 4 is provided with a section with a widened diameter forming a receptacle 40 into which the generator 5 can be inserted completely.

Figure 7:
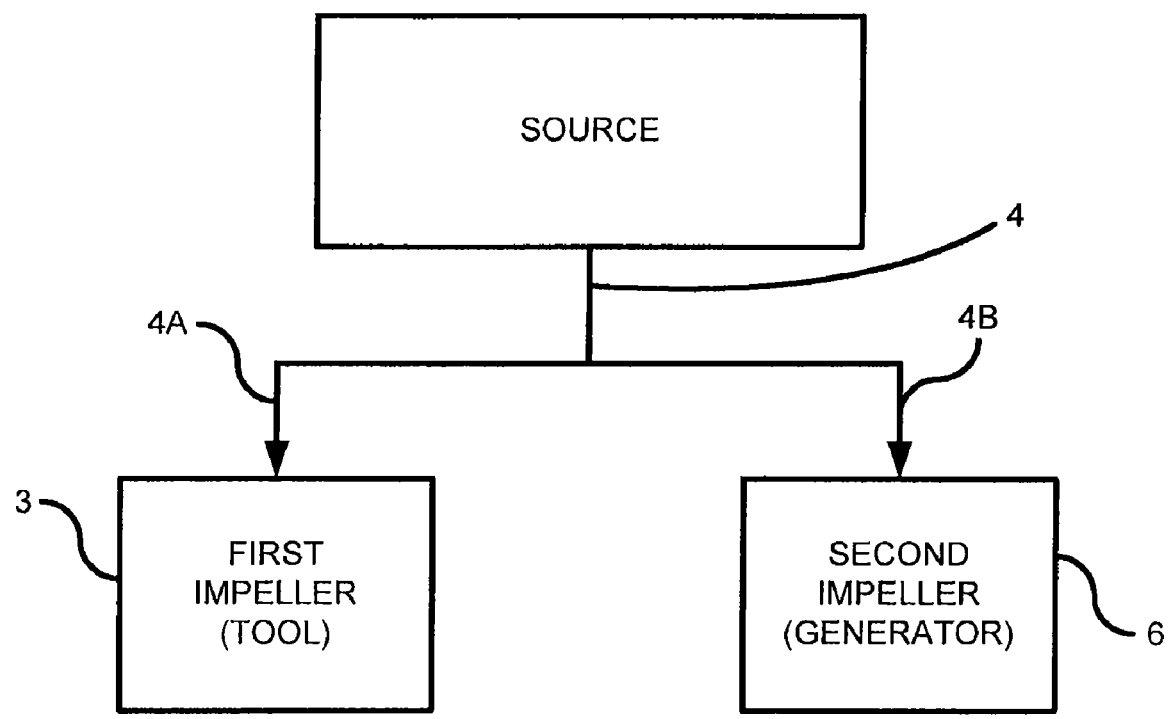
FIG. 7 shows a schematic illustration of a fluid-operated handheld element in which the first impeller and the second impeller are arranged in parallel rather than in series.

In alternative embodiments, it is of course possible to configure the first and second impellers in parallel rather than in series. For example, as shown schematically in FIG. 7, the first impeller 3 can be driven with fluid conveyed via a first branch 4A of the fluid line 4, with the second (generator) impeller 6 being driven with fluid conveyed by a second branch 4B.

An electric line 20 connects the generator 5 to a power consuming device or consumer 21, e.g., in the form of a lighting device 22. The lighting device 22 is accommodated in an opening 42 in the outer sleeve 31 and comprises at least one optical semiconductor element, in particular a light-emitting diode (LED), especially preferably a white LED. The light emitting diode preferably emits radiation with a wavelength in the range of approximately 380-700 nm for lighting the preparation site.

The lighting device 22 includes a lighting module 41 with the at least one optical semiconductor element. The lighting module 41 is situated in the light-emitting opening 42 in the outer sleeve 31 of the handheld element 1, such that at least most of the lighting module 41 and/or the optical semiconductor element is accommodated in the interior of the handheld element 1. Therefore, the lighting module 41 does not interfere with the handling of the handheld element 1. Due to the fact that the lighting module 41 is arranged in the immediate vicinity of the head part 28, no light guide is necessary for emitting the radiation onto the preparation site.

The at least one optical semiconductor element is accommodated in an interior of the lighting module 41 such that according to a preferred embodiment, the interior is sealed off hermetically with respect to the environment, so that the optical semiconductor element can be subjected to various cleaning and care measures, in particular sterilization, along with the handheld element 1 and can be protected from external influences, e.g., vapor, soiling, particles or cleaning agents, disinfectants or sterilizing agents. The hermetically sealed interior is formed by a base and a cap tightly sealed to the former, e.g., by welding. In addition, a transparent light-emitting window through which the light generated by the optical semiconductor element can pass is provided on the cap. Instead of the light-emitting window or subsequent thereto, other optical elements such as optical waveguides or lenses may also be provided. These optical elements may be designed as part of the lighting module 41 or as separate parts.

The lighting module 41 also consists of a fixture 43 which has an essentially cylindrical sleeve shape with a bore passing through it. The fixture 43 is preferably made of a material that does not conduct electricity. The socket and the cap are accommodated in the bore. In addition, a casting compound body 45 formed in particular by a synthetic resin, e.g., epoxy resin or silicone resin, is situated in the end of the fixture 43 facing the interior 44 of the handheld element 1. The casting compound body 45 surrounds the front end of the electric line 20 which is connected to the generator 5, in particular the section of the line 20 that is free of an insulating protective jacket. The casting compound body 45 also surrounds the electric contacts of the light-emitting diode. The line 20 and the contacts are inseparably joined together by the casting compound body 45. The line 20 and the contacts are preferably also soldered, welded or crimped (pinched) together. The casting compound body 45 also seals the lighting module 41 and the contacts.

A sealing element, e.g., a sealing ring is accommodated in a groove on the outer jacket of the fixture 43 and is clamped between the outer sleeve 31 of the handheld element 1 and the outer sleeve of the fixture 43. The sealing element seals the interior space 44 of the handheld element 1 and the components contained therein from the environment and prevents the penetration of particles, soiling, treatment media, cleaning agents, etc., into the handheld element 1 as well as preventing the escape of lubricant out of the interior of the handheld element 1. Such a seal may alternatively or additionally also be provided on the handheld element 1 itself.

In addition, fastening means are provided on the fixture 43, serving to attach the lighting device 22 to the handheld element 1. The fastening means comprise, for example, a flange 46 which is arranged on one end of the fixture 43 and the outer jacket of the fixture 43. The lighting module 41 is inserted into the light-emitting opening 42 such that the outside jacket of the fixture 43 is of such dimensions that it enters into a clamping connection with the outer sleeve 31 of the handheld element 1. To increase the frictional or clamping contact area with the outer jacket of the fixture 43, the outer sleeve 31 has a fastening element, e.g., in the form of protrusions, ring shoulders, etc., protruding into the interior space 44. If the fixture 43 is completely inserted into the light-emitting opening 42, then the flange 46 contacts the free end of the fastening element so that an additional fixation as well as accurate positioning of the lighting module 41 and the light-emitting opening 42 are achieved.

The fastening of the lighting module 41 in the light-emitting opening 42 is additionally achieved by the head section 28. The head section 28 has a protrusion 47 on its side facing the handle section 29, said protrusion 47 being insertable into the interior space 44 to connect the head section 28 to the handle section 29. The protrusion 47 is of such dimensions that, when inserted into the interior space 44, it contacts the lighting module 41 and presses it in the direction of the light-emitting opening 42 so that the lighting module 41 is fixedly secured in the light-emitting opening 42.

Power is supplied to the at least one optical semiconductor element via the electric pins or contacts of the semiconductor element, the electric line 20 and the carrier element 25, as described above, has additional electric contacts for connecting to the generator 5.

The lighting module 41 is preferably designed as a detachable or replaceable module, so it is replaced in particular via the interior space 44 of the handheld element 1 and the coupling opening 48. Alternatively, the lighting module 41 can be removed from the handheld element 1 through the light-emitting opening 42. The generator 5 is preferably also designed as a replaceable generator or as a generator cartridge, which can also be removed from the handheld element 1 through the coupling opening 48.

In both cases, the user must first detach the connecting device 2 and the outer sleeve part 31' from the handheld element 1. The connecting device 2 is preferably connected to components located in the interior of the handheld element 1 by means of multiple screws and can be removed from the handheld element 1 by loosening these screws. After releasing the outer sleeve part 31', the widened section of the fluid line 4 is exposed into which the generator 5 and/or the generator cartridge is/are inserted without any further means of fastening, so that the generator is easily removable from the fluid line.

To remove the lighting module 41, in the next step the user releases the carrier sleeve 49 which is part of the widened section of the fluid line 4, from the handheld element 1. To do so, screws held in a transverse bore in the outer sleeve 31 for axial fixation of the carrier sleeve 49 and the hollow screw 50 must be loosened. Then the head section 28 of the handheld element 1 must be separated from the handle section 29 so that the lighting module 41 which has been pressed into the light-emitting opening 42 through the head section 28 can be released out of the light-emitting opening 42. The user then exerts pressure on the lighting module 41 from the outside with his fingers or using a tool so that the lighting module is shifted into the interior space 44 of the handheld element 1. Finally, the user pulls the lighting module 41 and preferably also the line 20 out of the handheld element 1 via the coupling opening 48.

The generator 5 and the lighting module 41 are also inserted into the handheld element 1 via the interior space 44 and the coupling opening 48 in the opposite order from that described above for removal.

The detailed design of the generator 5 is explained below with reference to the two FIGS. 2 and 3.

The generator 5 comprises a generator shaft 15 on which are mounted the second impeller or generator impeller 6 and the rotor 16. The generator impeller 6 is designed as an excess pressure turbine, in which the dynamic pressure (flow pressure) of the drive fluid is approximately the same upstream and downstream from the impeller 6 and the static pressure or the enthalpy decrease. The impeller 6 is constructed for example as a Francis or Kaplan impeller or as an impeller which is similar to one of these two types of impeller. During operation, the generator impeller 6 is immersed completely in the drive fluid. As shown in FIG. 3 in particular, the second impeller 6 has several vanes 51 which are separated from one another by essentially U-shaped or V-shaped grooves cut, in particular milled, into the surface of the impeller 6. These grooves have approximately the same depth and width over their entire length. The drive fluid flows through these grooves so that the impeller 6 and thus the generator shaft 15 are set in rotation by the rotor 16.

The axis of rotation 13 of the generator impeller 6 running through the generator shaft 15 extends essentially axially between the two ends 11, 12 of the handheld element 1. The second impeller 6 is arranged in the handheld element 1 in such a way that the fluid flow is conveyed to it tangentially and/or radially. To reduce the weight, the generator impeller 6 is designed in a T shape, comprising a cylindrical sleeve-shaped central element 52 through which a bore passes for mounting the impeller 6 on the generator shaft 15, and a ring-shaped vane element 53 with the vanes 51 and grooves, the vane element 53 protruding away from the central element 52 at an angle. The vane element 53 is spaced at a distance from the central element 52 by a ring groove 54.

The rotor 16 is designed as a magnetic element 55, wherein the magnetic element 55 may be a single magnet or a segmented magnet having multiple pole pairs. The magnetic element 55 is preferably cylindrical in shape and is provided with a central bore through which the generator shaft 15 runs. The generator shaft 15 has two partial areas each having a different diameter, with the impeller 6 being arranged in the subarea having the larger diameter and the magnetic element 55 being arranged on the subarea having the smaller diameter. The purpose of the reduction in diameter of the generator shaft 15 in the area of the magnetic element 55 is to increase the power generation by the generator 5 by making available the greatest possible amount of magnetic material with at the same time the smallest possible diameter of the rotor 16 and thus the entire generator 5. The outside diameter of the magnetic element 55 is preferably about 3.4 mm to about 4.2 mm, especially preferably about 3.7 mm to about 3.9 mm. The inside diameter of the bore of the magnetic element 55 and accordingly the smaller diameter of the generator shaft 15 preferably amount to about 0.7 mm to about 1.2 mm, especially preferably about 0.9 mm to about 1.1 mm.

The essentially axial arrangement of the generator shaft 15 and the axis of rotation 13 of the second impeller 6 and the fastening of the second impeller 6 and the rotor 16 on a common shaft in the form of the generator shaft 15 allow these components to be supported by only two bearings and/or on just two bearing sites. According to the preferred embodiment depicted in FIGS. 2 and 3, the two bearing sites are provided on the respective ends of the generator shaft 15. The two bearing sites each comprise a friction bearing 17, 18. In addition, a spot bearing 19 for axial bearing support of the generator shaft 15 is provided on the bearing site facing the head section 28, said spot bearing 19 comprising a sphere 56 and the rounded front end of the generator shaft 15. The spot bearing 19 is arranged downstream from the second impeller 6 so that during operation of the generator 5, the fluid stream automatically forces the second impeller 6 and the generator shaft 15 connected to it in the direction of the spot bearing 19.

The stator 57 is arranged radially around the rotor 16. The stator 57 comprises a stator sleeve 58 made of plastic, preferably produced by injection molding or compression molding, at least one magnetic flux element 59, at least one coil 60 and electric contact elements 61 connected to at least one coil 60 for delivering the electric current generated by the generator 5 to the consumer 21. The stator sleeve 58 has a central bore in which the rotor 16 is accommodated and through which the generator shaft 15 passes. The two ends of the stator sleeve 58 are designed with double walls, with the coil 60, the electric contact elements 61 and optionally other electric or electronic components, e.g., a transformer or a rectifier being arranged at least to some extent in the ring-shaped intermediate spaces 62A, 62B running around the cylindrical central part of the stator sleeve 58 between the two walls. The at least one magnetic flux element 59 is situated between the two free ends of the wall sections of the stator sleeve 58 on the outside wall sections. To secure and protect the components, the stator sleeve 58, the at least one magnetic flux element 59, the at least one coil 60, the electric contact elements 61 and the electric or electronic components are cast with a casting compound, e.g., a synthetic resin, in particular epoxy resin or silicone resin.

If the second impeller 6 and the rotor 16 are induced to rotate by the drive fluid, then an electric alternating current is induced in the at least one coil 60 in a known manner by the alternating magnetic field of the magnetic element 55.

Between the generator impeller 6 and the stator 57 and/or the rotor 16, at least one guide element 14 is provided for tangential and/or radial deflection of the fluid stream onto the second impeller 6. As shown in FIG. 3 in particular, the guide element 14 has a plurality of spiral grooves or channels oriented toward the second impeller 6 and deflecting the fluid onto the impeller 6 and in particular into its vane grooves. The guide element 14 is also provided with a central bore so that the generator shaft 15 can pass through it.

The generator 5 is designed as a generator cartridge to facilitate replacement. To do so an outer shell 7 is provided, comprising an end plate or bearing shield 63 and a cylindrical generator sleeve 64 joined together by a thread. On the end opposite the thread, the generator sleeve 64 is sealed by a side wall, with an opening 65 which is surrounded by a ring-shaped wall being provided in the side wall. The side wall and the ring-shaped wall together form a receptacle 66 which serves as the first bearing site and into which the friction bearing 17 is inserted. The generator shaft 15 passes through the opening 65 and protrudes at its first end into the receptacle 66. In addition, several bores 67 are provided in the generator sleeve 64, forming a passage 10 and connecting the generator 5 and the interior of the outer shell 7 to the fluid conducting device 4 so that the drive fluid can flow to the second impeller 6.

The end plate 63 consists of a sleeve-shaped section which, when the end plate 63 is connected to the generator sleeve 64, surrounds the generator impeller 6, and a tapering section connected thereto and having a plurality of bores 68, which collect the drive fluid after it passes through the generator impeller 6 and discharge it to a section of the fluid line 4 having a smaller diameter. The second bearing site for the generator shaft 15 is provided at the center of the end plate 63. This bearing site comprises a receptacle 69 having a bore with different diameters, wherein the ball 56 of the spot bearing 19 sit in the first bore section having the smaller diameter facing the head section 28 and the second friction bearing 18 sits in the second bore section having the larger diameter facing away from the head section 28. The generator shaft 15 protrudes into the receptacle 69, in particular through the bore section having the larger diameter as far as into the bore section having the smaller diameter.

The generator 5 and/or the generator cartridge is accommodated in a section of the fluid conducting device 4 that has an enlarged diameter and forms a receptacle 40. The section of the fluid conducting device 4 having the enlarged diameter comprises the carrier element 25 and the carrier sleeve 49 connected thereto. The generator 5 is inserted into the interior space of the carrier sleeve 49 forming the receptacle 40 and is secured by the carrier element 25 that can be placed on the generator 5 and the carrier sleeve 49.

The carrier sleeve 49 has a section with a reduced diameter on its end facing the head section 28, such that a hollow screw 50 is arranged in that section. The hollow screw 50 is connected by a thread to a section of the fluid line 4 which is designed as a pipeline having a smaller diameter and passes through an opening in the carrier sleeve 49. A sealing element mounted on the hollow screw 50 prevents the drive fluid from escaping out of the fluid line 4. After passing through the generator impeller 6, the drive fluid thus flows through the end plate 63 and the inside bore in the hollow screw 50 and goes through the section of the fluid line 4 designed with a smaller diameter to the first impeller 3.

The outer shell 7 of the generator, in particular the generator sleeve 64, is arranged at least in a section at a distance away from the inside wall 8 of the fluid line 4 surrounding the generator outer shell 7, thus forming a fluid channel 9 for conducting the fluid stream. The fluid channel 9 opens into a passage 10 in the form of multiple bores 67 for conducting the fluid stream to the second impeller 6. The passage 10 is preferably arranged around the conducting element 14 so that drive fluid flowing axially in the fluid channel 9 enters the guide element 14 directly and is deflected by it into an optimal tangential and/or radial direction of flow for the generator impeller 6.

The carrier element 25 is a plastic sleeve having an inside bore manufactured preferably by injection molding. The carrier element 25 is connected to the generator 5 and to the carrier sleeve 49 at its first end and to the connecting device 2 at its second end. The drive fluid flows from the connecting device 2 through the inside bore of the carrier element 25 into the fluid channel 9 so that the carrier element 25 is designed as part of the fluid conducting device 4.

In addition, parts of the electric connection between the generator 5 and the consumer 21 are provided on the carrier element 25, so that the carrier element also serves as a plug-in circuit board. Electric contact elements 61, e.g., wires, electric lines and contact pins 26 extend from the at least one coil 60 of the stator 57 through the stator sleeve 58. In addition, the contact pins 26 protrude through openings in the stator sleeve 58 and in the generator sleeve 64 into the carrier element 25 on which an electrically conducting spring contact 27 is provided. The spring contact 27 is connected to the electric line 20 to which the consumer 21 is also connected. The end of the line 20 facing the connecting device 2 is connected to the carrier element 25 by means of a casting material, e.g., synthetic resin, in particular epoxy resin or silicone resins, preferably applied in vacuo, for the purpose of providing a secure connection and a stable seal.

Figure 3:
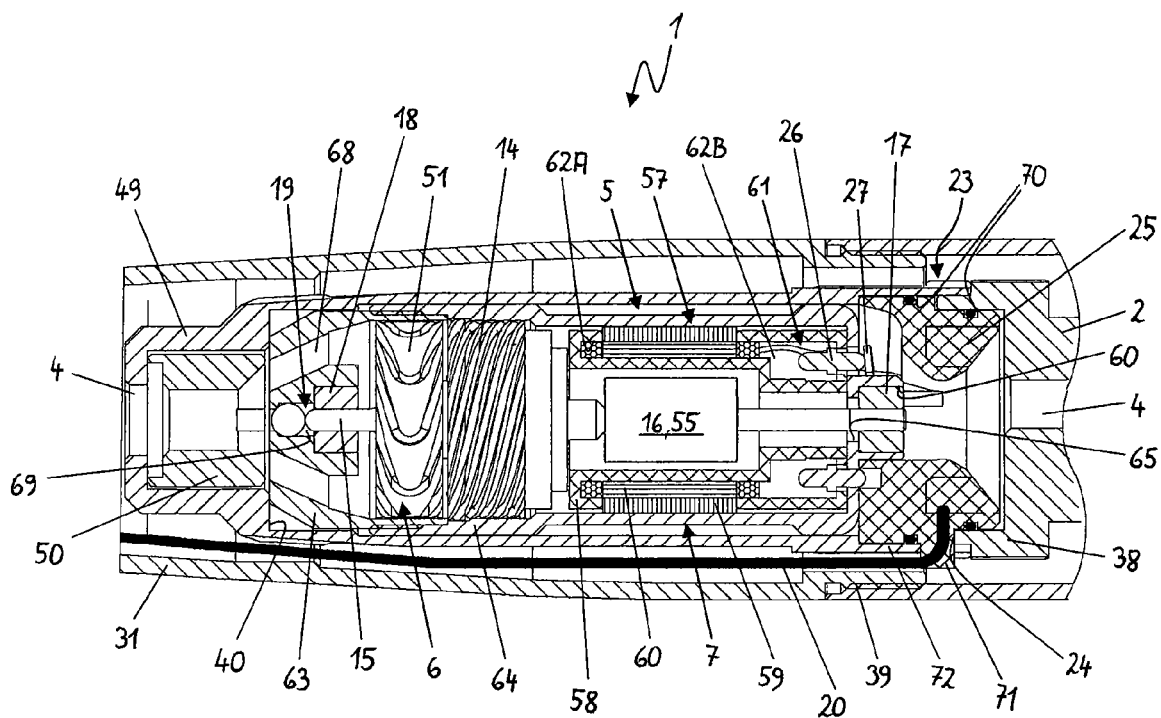
FIG. 3 shows an enlarged diagram of the generator from FIG. 1 in a second sectional plane, in particular to illustrate the electric components of the generator.

As shown in FIG. 3 in particular, the electric line 20 comes out of the carrier element 25 and thus out of the fluid conducting device 4. The electric line 20 is accommodated in a protrusion 71 on the carrier element 25 which protrudes through the carrier sleeve 49. To prevent the drive fluid from flowing out of the fluid line 4 at the passage point 24 of the electric line 20 in the wall 72, a sealing device 23 is provided, preferably being arranged on the carrier element 25. The sealing device 23 comprises one or more sealing elements, e.g., O-rings which are accommodated in the grooves 70 of the carrier element 25 beside the protrusion 71 and which contact the connecting device 2 and the carrier sleeve 49 in the installed state.

Figure 4:
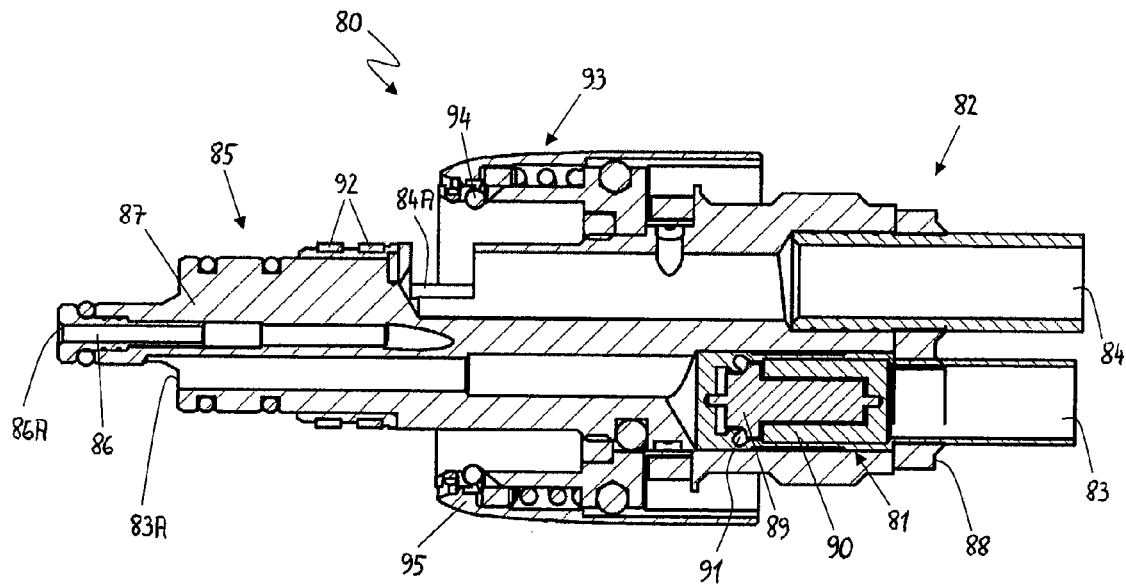
FIG. 4 shows a second embodiment of a fluid-operated handheld element with a generator, which is configured as a coupling or adapter for the connection to a handpiece or a contra-angle handpiece.
Figure 5:
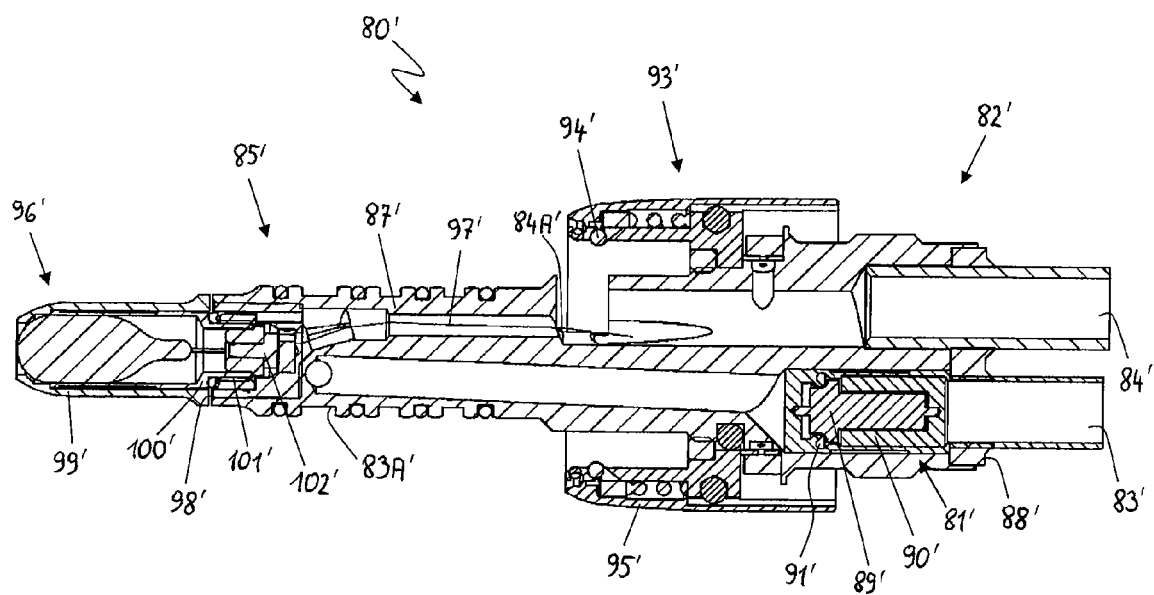
FIG. 5 shows a third embodiment of a fluid-operated handheld element with a generator, which is configured as a coupling or adapter with a lighting device for the connection to a handpiece or a contra-angle handpiece.

In FIGS. 4 and 5, two alternative example embodiments are illustrated of fluid-operated medical, in particular dental, handheld elements with a generator 81, 81', in which the handheld element is constructed as an adapter or coupling device 80, 80'. The adapter or the coupling device 80, 80' connects a medical, in particular dental, handpiece or contra-angle handpiece with a supply tube and/or with a control and/or supply device and/or with one or more media sources, so that a medium or several media, for example water, compressed air or compressed gas, light etc., and/or control signals are able to be conducted between the handpiece or contra-angle handpiece and the supply tube and/or the control- and/or supply device and/or the media sources. To do this, the adapter or the coupling device 80, 80' has one or more media passageways, for example bores, channels, lines or grooves which respectively connect lines in the handpiece or contra-angle handpiece with lines of the supply tube, the control- and/or supply device and/or the media sources.

To connect the coupling device 80, 80' with the handpiece or contra-angle handpiece, a releasable locking device 93, 93' is provided, which comprises one or more locking elements 94, 94' which cooperate with corresponding counter-elements of the handpiece or contra-angle handpiece, and also an actuating element 95, 95', for example a sliding sleeve, to actuate the at least one locking element 94, 94'. The sliding sleeve also serves as an external or grip sleeve of the coupling device 80, 80'.

The coupling device 80, 80' has an elongated shape with a first end and a second end, in which at one of the two ends a connection device 82, 82' is provided for releasable connection with the supply tube and/or with the control- and/or supply device and/or with the media sources and at the other end a connection device 85, 85' is provided for releasable connection with the handpiece or contra-angle handpiece. The connection devices 82, 82', 85, 85' can be basically constructed as a plug-, screw-, clamping- or rotary coupling, in which in accordance with the embodiments according to FIGS. 4 and 5, the connection devices 82, 82' are constructed as plug couplings and the connection devices 85, 85' are constructed as plug-rotary couplings.

Two fluid-conducting devices or fluid lines 83, 84 and 83',84' can be seen at the connection device 82, 82', which lines extend up to the connection device 85, 85'. The line 83, 83' conveys a fluid, in particular compressed air, to the handpiece or contra-angle handpiece, and the line 84, 84' conveys the fluid away from the handpiece or contra-angle handpiece. Alternatively, the connection device 82, 82' can also only have the line 83, 83' for conveying the fluid to the handpiece or contra-angle handpiece. On the connection device 82, 82' a further fluid line is provided in particular for conducting water into the handpiece or contra-angle handpiece, but this further fluid line not being able to be seen due to the sectional planes which have been selected in FIGS. 4 and 5. All fluid lines have respectively short tube sections which project over the end face 88, 88' of the connection device 82, 82' and are held in bores or in channels of the coupling device 80, 80'.

The connection device 85, 85' comprises a rod- or pin-shaped cylindrical body 87, 87' for connection to the handpiece or contra-angle handpiece, in particular for mounting in a coupling mounting, for example a coupling tube of the handpiece or contra-angle handpiece. On the connection device 85, 85', the two fluid lines 83, 84 and 83', 84' can be seen and in the case of the connection device 85 the fluid line 86 for the water, centrally arranged in the coupling pin 87, with the associated opening 86A. The line 83 terminates in an opening 83A in the region of a ring-shaped step or shoulder of the coupling pin 87, the line 83' opens into an annular channel 83A' on the covering surface of the coupling pin 87'. The line 84, 84' terminates in an opening 84A, 84A', at the base of the coupling pin 87, 87'. On the covering surface of the coupling pin 87, 87', in addition several annular grooves are provided with sealing elements, for example O-rings, for sealing the individual media passages.

The generator 81, 81' is constructed such that, or is arranged in the coupling device 80, 80' such that at least a portion of its impeller 89, 89' is held in the driving air line 83, 83'. Particularly preferably, the entire impeller 89, 89' is held in the driving air line 83, 83', so that the impeller 89, 89' is able to have the drive fluid flowing completely around it, or is immersed therein. Preferably, further components of the generator 81, 81', for example at least parts of the rotor or of the stator or of the sleeve 90, 90' surrounding the generator 81, 81' or a part thereof, are also arranged in the driving air line 83, 83' for cooling the generator 81, 81'. The sleeve 90, 90' protects the generator 81, 81' from contamination and can be part of a cartridge surrounding the entire generator 81, 81'.

On the generator 81, 81' or as part of the generator 81, 81', at least one guide element 91, 91' is provided, which deflects or alters the direction of the drive fluid in such a way that the impeller 89, 89' of the generator 81, 81' is able to be flowed against radially and/or tangentially. The guide element 91, 91' comprises for example furrows or grooves which are preferably provided in or on the sleeve 90, 90'. The drive fluid flows before the deflection through the guide element 91, 91' substantially axially, with respect to the longitudinal axis of the coupling device 80, 80', through the fluid line 83, 83'.

The blades of the impeller 89, 89' are constructed or formed, in particular have a curved or bent shape such that they alter the direction of flow of the drive fluid. Preferably, they bring about a substantially axial flowing out or on of the fluid, in relation to the longitudinal axis of the coupling device 80, 80', in the fluid line 83, 83'. Instead of the impeller 89, 89' or in addition to the impeller 89, 89', further components can be provided on the generator 81, 81' or joining onto the generator 81, 81', which, in particular on flowing through the generator 81, 81' and/or after flowing through the generator 81, 81', bring about a substantially axial further flowing of the drive fluid.

Through the incorporation of the entire impeller 89, 89' into the fluid line 83, 83', its complete flowing around by the drive fluid and the radial and/or tangential flowing against of the impeller 89, 89', a particularly high output generation of the generator 81, 81' is achieved.

As already mentioned above, the coupling device 80, 80' is able to be detachably connected with a medical, in particular dental, handpiece or contra-angle handpiece, in which the handpiece or contra-angle handpiece preferably comprises a fluid-operated drive unit, in particular an impeller which is able to be driven by means of compressed air, so that the handpiece or contra-angle handpiece is constructed as a turbine handpiece which is operated by compressed air. Through the connection of the adapter or of the coupling device 80, 80' with a handpiece or contra-angle handpiece, the resulting handheld element, which comprises two impellers, may be referred to as a handpiece assembly.

Such a turbine handpiece has a front region or head section, which matches the head section 28 of the handheld element 1 of FIG. 1, in which therefore in particular a tool receptacle is arranged which is accessible through a tool opening, which receptacle is accommodated at least partially in a hollow shaft and is movably mounted, in particular through two ball bearings. The impeller is fastened on the hollow shaft, said impeller being able to be set in rotation jointly with the hollow shaft and the tool receptacle. The compressed air is supplied to the impeller via a first fluid conducting device or driving air line, and after the passage of the impeller is removed again via a second fluid conducting device or return air line.

Through the connection of the turbine hand piece with the coupling device 80, 80', the fluid line 83, 83' of the coupling device 80, 80' is connected with the driving air line of the turbine hand piece and the fluid line 84, 84' of the coupling device 80, 80' is connected with the return air line of the turbine hand piece. The impeller 89, 89' of the generator 81, 81' and the impeller of the turbine hand piece are therefore arranged serially or, in relation to the fluid flow, one behind the other. In other words, the two impellers are arranged on or along a single fluid line, which is divided into two sections which are able to be separated from each other or connected with each other. This single, shared fluid line guides the drive fluid firstly to one impeller, preferably the impeller 89, 89' of the generator 81, 81', and then to the other impeller, preferably the impeller of the turbine hand piece.

In order to make possible such a serial operation of the two impellers and in particular to obtain a sufficient power output or a sufficient torque of both impellers, in a preferred example embodiment the impeller 89, 89' of the generator 81, 81' is constructed as an excess pressure turbine or reaction turbine, for example as a Francis or Kaplan turbine or as a turbine which is similar to these two types of turbine. Turbines or impellers in which the static pressure is greater at the entry into the impeller than at the exit are designated as excess pressure turbines or a reaction turbines. In addition, the impeller of the turbine hand piece is preferably constructed as an equal pressure, free-jet or action turbine, for example as a Pelton impeller or as an impeller similar to a Pelton impeller, in which the static pressure at the impeller entry and at the impeller exit is equally great, so that primarily the dynamic pressure or the kinetic energy of the drive fluid drives the impeller.

According to the embodiment in accordance with FIG. 4, the generator 81 is connected via two electric lines or cables with two electric contacts 92, which are arranged on the connecting device 85 facing the handpiece or contra-angle handpiece. For the purpose of simple manufacture, the electric lines or cables run at least partially in fluid lines, for example the lines 83, 84. The two contacts 92 are preferably constructed as contact rings which surround the coupling pin 87 on its covering surface and are part of sliding contacts. Accordingly, electric cooperating contacts are provided on the fluid conducting device, which cooperating contacts contact the electric contacts 92 so that the current generated by the generator 81 can be supplied to one or more electric consumers in or one the handpiece or contra-angle handpiece, for example a lighting device, which preferably comprises at least one light-emitting diode, a laser light generator or a control or regulating device.

In contrast to this, in the coupling device 80' according to FIG. 5, at least one electric consumer, in particular a lighting device 96' with at least one light-emitting diode or an incandescent bulb is provided in or on the coupling device 80'. The lighting device 96' is preferably arranged on the coupling pin 87', in particular on its free end facing the handpiece or contra-angle handpiece, in a mounting 98', so that the light generated by the lighting device 96' is able to be transferred directly to the handpiece or contra-angle handpiece, for example is able to be coupled with a light guide. The connection between the generator 81' and the electric consumer takes place via two electric lines or cables 97', which again run at least partially in fluid lines, for example the lines 83', 84'. In order to prevent an unintentional outflow of the fluid from the line 83', 84' holding the electric lines 97', one or more sealing elements are provided respectively in the region of the entry point of the electric lines 97' into the line 83', 84' and in the region of the exit point of the electric lines 97' from the line 83', 84'.

The lamp or light-emitting diode of the lighting device 96' is preferably surrounded by a sleeve 99', in particular a plastic sleeve, for mechanical protection and for protection from contamination. The lighting device 96' additionally comprises a holder 100', which is connected via a fastening device 101', for example a thread or a plug connection, directly or indirectly via a bush with the mounting 98' of the coupling pin 87'. For connection with the electric lines 97', the lighting device 96' comprises two electric contacts which are formed for example by the holder 100', by one or two metal pins 102', spring contacts or bushes. The electric lines 97' are connected with the electric contacts of the lighting device 96' directly or indirectly via parts of the mounting 98'.

Figure 2:
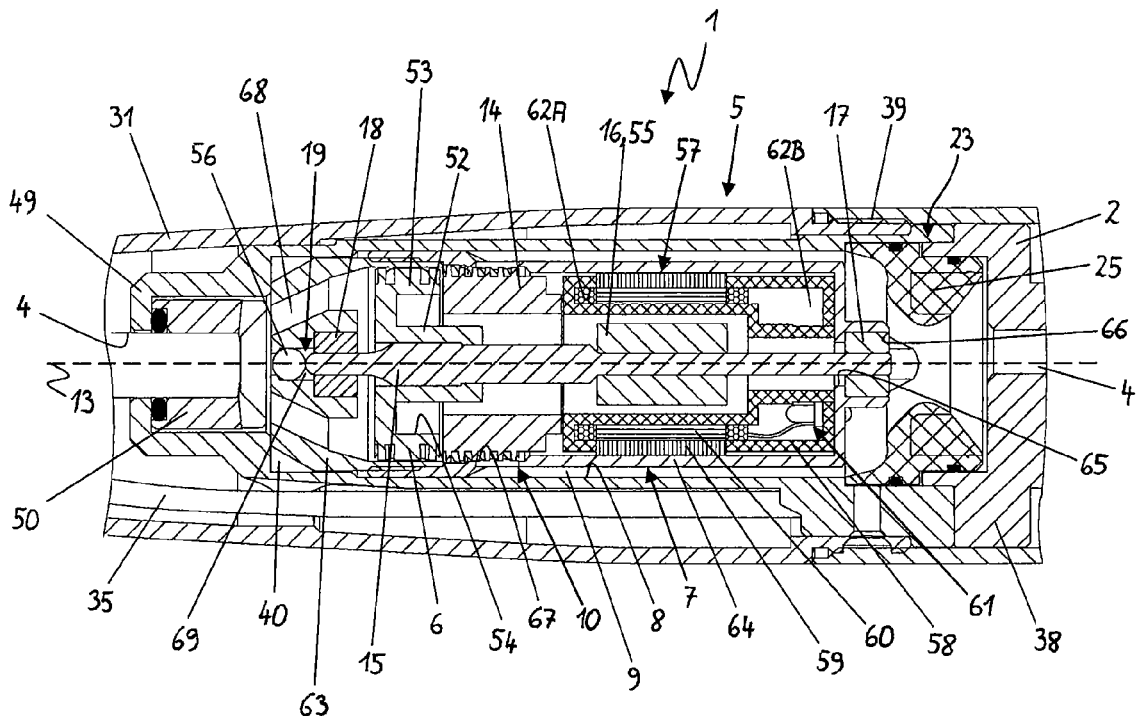
FIG. 2 shows an enlarged diagram of the generator from FIG. 1 in a first sectional plane, in particular to illustrate the fluid conducting device.
Figure 6:
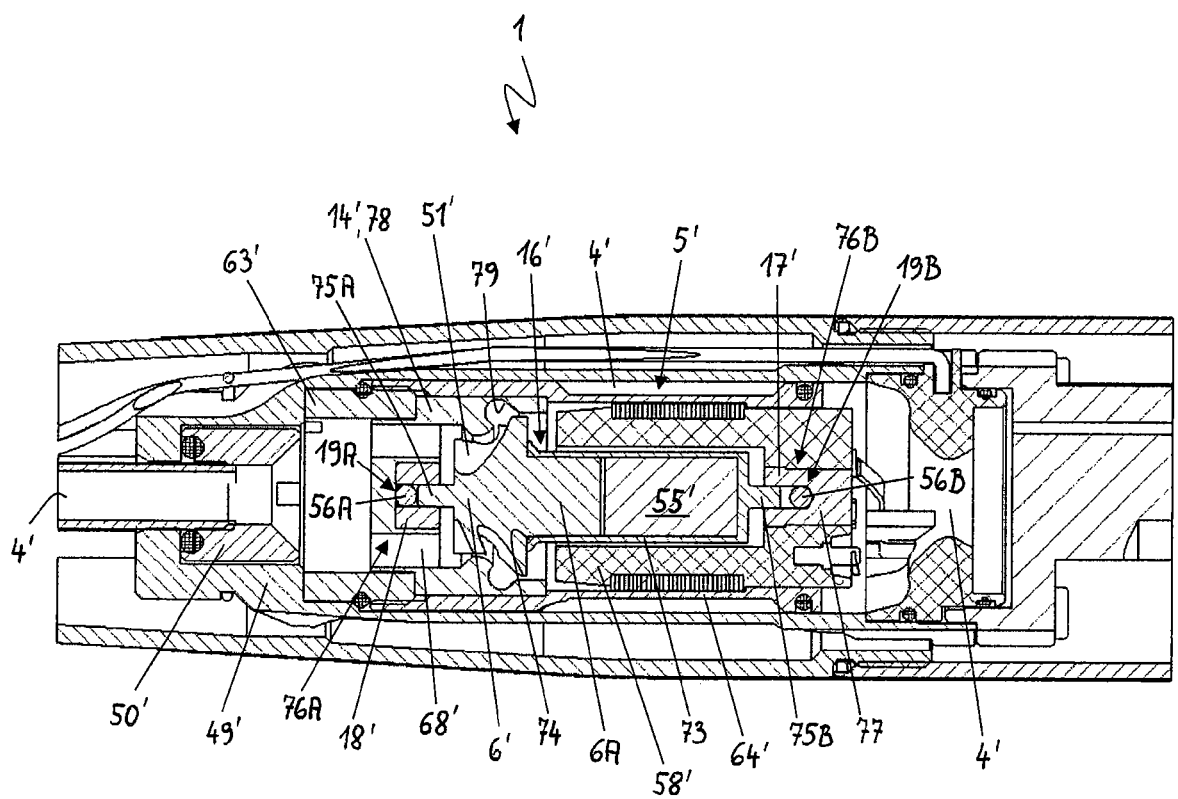
FIG. 6 shows an alternative embodiment of a generator for a fluid-operated handheld element.

The generator 5' illustrated in FIG. 6 is similar in its structure to the generator 5 illustrated in FIGS. 2 and 3 and described in detail above, and can be incorporated, instead of this generator 5, for example into a handheld element 1 according to FIG. 1 or into an adapter or a coupling device 80, 80' according to FIGS. 4, 5. In the following, primarily therefore the features are described which differentiate the generator 5' from the generator 5.

In order to be able to better protect the rotor 16' of the generator 5' with the rotor magnet 55', which is preferably constructed as a neodymium-iron-boron magnet, from external influences such as cleaning agents, water vapour or contamination, the rotor magnet 55 is surrounded by a protective sleeve 73, which consists of a non-magnetic material, for example, steel or plastic.

The cylindrical rotor magnet 55' is held completely in the cup-shaped protective sleeve 73. Joining on to the rotor magnet 55' and likewise at least partially arranged in the protective sleeve 73 is a shaft-shaped extension 6A of the second impeller 6', in which the extension 6A has a smaller diameter than the second impeller 6'. The extension 6A projects through the single opening 74 of the sleeve 73 into the latter, the sleeve 73 being welded or pressed with the shaft-shaped extension 6A and preferably being additionally glued.

At the end of the sleeve 73 lying opposite the opening 74, a stub-shaped shaft piece 75B is provided, preferably as an integral part of the sleeve 73, which serves for the rotatable mounting of the rotor 16' on a bearing site 76B. This bearing site 76B is at least partially formed by the stator sleeve 58' of the generator 5', in particular through a bore or mounting in the stator sleeve 58', and comprises a friction bearing 17' and a spot bearing 19B for the axial mounting of the rotor 16'. The friction bearing 17' comprises a bearing bush 77 fastened in the mounting of the stator sleeve 58', with a blind-end bore, into which the shaft piece 75B projects and in which, between the shaft piece 75B and the base of the blind-end bore, the ball 56B of the spot bearing 19B is situated. The ball 56B of the spot bearing 19B is preferably made from ceramic material or has a ceramic coating. The protective sleeve 73, in particular the shaft piece 75B, is preferably coated, for example with a titanium-nitride layer or with a nickel layer (chemical nickel), in order to harden the surface of the shaft piece 75B.

At the opposite end of the rotor 16', a second, short, stub-shaped shaft piece 75A is provided, preferably likewise coated like shaft piece 75B, which shaft piece 75A is rotatably mounted on a further bearing site 76A. The bearing site 76A again comprises a friction bearing 18' and a spot bearing 19A with a ball 56A which is ceramic or coated with ceramic. The bearing site 76A is formed by a mounting with a blind-end bore of the bearing plate or end plate 63', in which the ball 56A and the shaft 75A are held.

The entire rotor 16' including the second impeller 6' and the rotor magnet 55' is therefore mounted in a rotary manner exlusively by the friction bearings 17', 18'. The use of friction bearings has the advantage, already described above in detail, that the risk of failure of the generator 5' by a standstill of the rotor 16' and of the generator shaft, formed by the two shafts 75A, 75A, through contamination and in particular through lubricant for lubricating components of the handheld element adhereing to the generator bearings is greatly reduced or eliminated.

The generator 5', in particular the second impeller 6', are surrounded by a guide sleeve 78 which joins on to the bearing plate or end plate 63' and is situated inside the carrier sleeve 49' for the generator 5'. The guide sleeve 78 has at least one spiral-shaped furrow or groove 79 and therefore serves as a guide element 14' for the tangential and/or radial deflection of the fluid stream onto the second impeller 6'. The at least one groove 79 is connected with the fluid conducting device 4', in which the drive fluid for the generator impeller 6' is guided, via one or more bores in the generator sleeve 64'. The fluid conducting device 4' is formed in the region of the generator 5' by a gap between the carrier sleeve 49' and the generator sleeve 64', which is flowed through by the drive fluid axially, in relation to the longitudinal axis of the generator 5' or of the handheld element 1.

The second impeller 6' is constructed as an excess pressure- or reaction turbine, in particular as a Francis turbine, and is held completely in the fluid conducting device 4', so that during operation it is completely immersed in the drive fluid. The vanes 51' of the second impeller 6' are constructed or shaped, in particular have a curved or bent shape, such that they alter the direction of flow of the drive fluid. Preferably, they bring about a substantially axial flow out or on of the fluid, in relation to the longitudinal axis of the generator 5' or of the handheld element 1, through the fluid conducting device 4', in particular through the bores 68' of the end plate 63', through the hollow screw 50' and the fluid line adjoining thereto. After leaving the generator 5', the drive fluid flows to the first impeller 3 (see FIG. 1), which is arranged on or along the fluid conducting device 4' serially to the second impeller 6'.

A serial arrangement of the first impeller 3 and the second impeller 6 is provided in some embodiments so that drive fluid conducted in the fluid conducting device 4 is supplied first to one of the impellers 3, 6 and then to the other of the impellers 3, 6. In relation to the flow direction of the drive fluid, the second impeller 6 is arranged upstream of the first impeller 3. In this way, drive fluid is supplied first to the second impeller 6 via a first section of the conductive device 4 and then to the first impeller 3 via a second section of the conducting device 4.

As shown for example in FIG. 2, the second impeller 6 has an axis of rotation 13. In the illustrated embodiment, the axis of rotation for the rotor of the generator 5 is coincident with the axis 13. As can be seen at the right side of FIG. 2, the center of the first section of the fluid conducting device 4 is generally parallel to but offset from the axis 13. Therefore, at least a part of a center axis of the first section of the fluid conducting device 4 and at least one of the second impeller's axis of rotation 13 and the generator's axis of rotation are arranged substantially in parallel and spatially offset to each other (or one another).

This application is not limited to the exemplary embodiments described here but instead comprises all possible embodiments which do not alter the basic principles. All the features of all the embodiments which are described and illustrated are also able to be combined with each other or exchanged for each other.

It is thus of course possible for the generator impeller and the magnetic element of the rotor to be designed so they contact one another without a distance between them. Alternatively, the generator impeller or parts thereof may be made of a magnetic material so that the impeller assumes both the driving function as well as the function of the magnetic element of the generator.

Instead of inducing rotation in the magnetic element, it is also possible to connect one or more coils to the impeller and to rotate them and to design the magnetic element so as to be non-rotatable and as part of the stator.

As an alternative to the embodiment depicted in FIG. 1, in which the drive fluid first flows through the generator 5 and then the first impeller 3 which drives the tool, it is of course also possible for the drive fluid to first be supplied to the impeller driving the tool and then to be supplied to the generator through a fluid conducting device. The fluid conducting device may be formed at least partially by the outer sleeve of the handheld element.

In addition to supplying electric power to a lighting device, the generator may also serve as a power source for one or more other consumers, e.g., for a diode laser, an ultrasonic generator or a microwave generator, an analgesia device, for measurement sensors, e.g., for measuring temperatures, acceleration, torque, rotational speed or sound volume, for microphones, for actuators, e.g., piezoelectric elements for dampening vibration, for circuits for processing or preparing data or measured values, for control and/or regulating circuits, for data transmission devices and transmitters, for devices for recognizing tools that can be connected to the handheld element or for instruments and displays.

In addition or as an alternative to dissipation of heat via the drive fluid, the handheld element may also be provided with a cooling device for dissipating the heat generated by the generator. The cooling device may consist of, for example, active or passive cooling elements, so-called heat pipes having a vaporizable and condensable heat transfer medium contained in their interior, thermal conducting pastes or pads or other known thermal conducting devices.

In view of the many possible embodiments to which the disclosed principles may be applied, it should be recognized that the illustrated embodiments are only preferred examples and should not be taken as limiting in scope. Rather, the scope of protection is defined by the following claims, and we therefore claim all that comes within the scope and spirit of these claims.

What is claimed is:

1. A fluid-operated medical or dental handheld element comprising a connecting device for connecting the handheld element to a fluid source, a fluid conducting device arranged between the connecting device and a first impeller for conveying a fluid stream toward or away from the first impeller, wherein the first impeller can be induced by fluid to rotate and is connectable to a tool so that the tool can be induced by the first impeller to execute a working motion, a generator for generating electric power, wherein the generator comprises a second rotatable impeller positioned in series relative to the first impeller and driveable by at least a substream of the fluid stream conveyable in the fluid conducting device, an outer sleeve within which at least the generator is located, the outer sleeve serving as a return passageway which conveys the drive fluid that has passed the second impeller and the first impeller towards the connecting device, wherein the second impeller is constructed as an excess pressure turbine or reaction turbine driveable by the static pressure or the enthalpy decrease of the drive fluid while the dynamic pressure or the kinetic energy of the drive fluid is approximately the same upstream and downstream from the second impeller, and wherein the first impeller is constructed as an equal pressure turbine or action turbine driveable by the dynamic pressure or the kinetic energy of the drive fluid while the static pressure or the enthalpy of the drive fluid is approximately the same upstream and downstream from the first impeller.

2. The handheld element according to claim 1, wherein the generator is at least partially accommodated in the fluid conducting device.

3. The handheld element according to claim 1, wherein the handheld element has an elongated shape with a first end and a second end, wherein the axis of rotation of the second impeller extends substantially axially between these two ends and wherein the second impeller is arranged in the handheld element in such a way that the fluid stream can flow toward the second impeller tangentially with respect to the axis of rotation of the second impeller.

4. The handheld element according to claim 1, wherein the handheld element has an elongated shape with a first end and a second end, wherein the fluid conducting device extends generally axially between the two ends of the handheld element at least for a section so that the fluid stream can be conveyed generally axially therein, and wherein at least one guide element is provided for deflecting the generally axial fluid stream onto the second impeller.

5. The handheld element according to claim 1, wherein the generator comprises a rotatable generator shaft on which the second impeller and a rotor are arranged, wherein at least one bearing is provided for bearing support of the generator shaft, and wherein the bearing does not require any supply of lubricant to be introduced from outside the handheld element when in the installed state, the bearing comprising at least one of a friction bearing, a hydro bearing, an air bearing and a roller bearing and having at least one ceramic material provided for bearing support of the generator shaft.

6. The handheld element according to claim 1, comprising a spot bearing for axial bearing support of the generator shaft such that the spot bearing is arranged downstream from the second impeller.

7. The handheld element according to claim 1, wherein an electric line for connecting the generator to a power consuming device such that the electric line passes through a wall of the fluid conducting device, and wherein a sealing device is provided for sealing the passage of the electric line through the fluid conducting device.

8. The handheld element according to claim 7, further comprising a carrier element, wherein the sealing device is arranged on a carrier element on which electric contact elements are provided for connecting the electric line to the generator.

9. The handheld element according to claim 8, wherein the carrier element is designed as part of the fluid conducting device for conducting the fluid stream to the generator.

10. The handheld element according to claim 1, further comprising a lighting device which is connected to the generator and can be supplied with electric power by the generator, the lighting device having a hermetically encapsulated interior space in which at least one optical semiconductor element is arranged, so that the optical semiconductor element can be subjected to numerous sterilizations and can be protected from external influences like vapor or sterilizing agents during sterilization.

11. The handheld element according to claim 1, wherein the lighting device is detachably coupled to the handheld element.

12. The handheld element according to claim 1, wherein the first impeller is arranged in the handheld element.

13. The handheld element according to claim 1, wherein the handheld element is a handpiece having a straight form or having a curved form, and wherein the first impeller and the second impeller are arranged in the handpiece.

14. A fluid-operated medical or dental handheld element comprising a connecting device for connecting the handheld element to a fluid source, a first impeller that can be induced by fluid to rotate and is connectable to a tool so that the tool can be induced by the first impeller to execute a working motion, a generator for generating electric power, wherein the generator comprises a second impeller that can be induced to rotate by fluid, and with a fluid conducting device for conveying a fluid stream from the connecting device to the first and second impeller, wherein a serial arrangement of the first and second impeller is provided, so that the drive fluid which is conducted in the fluid conducting device is supplied first to one of the first and second impellers and then to the other of the first and second impellers, wherein in relation to the flow direction of the drive fluid, the second impeller is arranged upstream of the first impeller, so that the drive fluid is supplied first to the second impeller and then to the first impeller, and wherein the handheld element comprises an outer sleeve within which at least the generator is located, the outer sleeve serving as a return passageway which conveys the drive fluid that has passed the second impeller and the first impeller to the connecting device.

15. The handheld element according to claim 14, wherein the second impeller is accommodated completely in the fluid conducting device so that the fluid immerses and is caused to flow around the second impeller.

16. The handheld element according to claim 14, wherein the entire generator is accommodated in the fluid conducting device.

17. The handheld element according to claim 14, comprising a drive fluid flow path segment for the drive fluid that is substantially axial in relation to the longitudinal axis of the handheld element, through the handheld element and with a tangential flow against the second impeller.

18. The handheld element according to claim 17, comprising a guide element that tangentially deflects the generally axial drive fluid stream onto the second impeller.

19. The handheld element according to claim 17, wherein the second impeller is configured for deflection of the tangential drive fluid stream in a substantially axial direction, with respect to the longitudinal axis of the handheld element.

20. The handheld element according to claim 14, wherein the second impeller is constructed as an excess pressure turbine or reaction turbine.

21. The handheld element according to claim 20, wherein the first impeller is constructed as an equal pressure turbine or action turbine.

22. The handheld element according to claim 14, wherein the generator comprises a rotor magnet which is held in a protective sleeve of a non-magnetic material.

23. The handheld element according to claim 14, further comprising at least one friction bearing for a rotary mounting of the rotor of the generator.

24. The handheld element according to claim 14, comprising at least one spot bearing for the axial mounting of a rotor of the generator.

25. The handheld element according to claim 14, wherein the return passageway, which conveys the drive fluid that has passed the second impeller and the first impeller to the connecting device, passes the generator.

26. A fluid-operated medical or dental handheld element, comprising
a connecting device for connecting the handheld element to a fluid source,
a first impeller that can be induced by fluid to rotate and is connectable to a tool so that the tool can be induced by the first impeller to execute a working motion,
a generator for generating electric power, wherein the generator comprises a second impeller that can be induced to rotate by fluid,
a fluid conducting device for conveying a fluid stream from the connecting device to the first and second impeller,
an outer sleeve within which at least the generator is located,
wherein a serial arrangement of the first and second impeller is provided, so that the drive fluid which is conducted in the fluid conducting device is supplied first to one of the first and second impellers and then to the other of the first and second impellers, wherein in relation to the flow direction of the drive fluid, the second impeller is arranged upstream of the first impeller, so that the drive fluid is supplied first to the second impeller via a first section of the fluid conducting device and then to the first impeller via a second section of the fluid conducting device,
wherein the outer sleeve serves as a return passageway which conveys the drive fluid that has passed the second impeller and the first impeller to the connecting device,
wherein the second impeller has an axis of rotation,
wherein the generator comprises a rotor having an axis of rotation,
wherein the first section of the fluid conducting device which supplies the drive fluid to the second impeller has a centre axis, so that the first section of the fluid conducting device extends between the connecting device and the second impeller along said centre axis, and
wherein at least a part of the centre axis of the first section of the fluid conducting device and at least one of the axis of rotation of the second impeller and the axis of rotation of the rotor of the generator are arranged substantially in parallel and spatially offset to each other.

27. The handheld element according to claim 26, wherein at least a part of the second section of the fluid conducting device which supplies the drive fluid to the first impeller is arranged at an angle with respect to centre axis of the first section of the fluid conducting device.

28. The handheld element according to claim 26, wherein the second impeller is constructed as an excess pressure turbine or reaction turbine driveable by the static pressure or the enthalpy decrease of the drive fluid while the dynamic pressure or the kinetic energy of the drive fluid is approximately the same upstream and downstream from the second impeller, and wherein the first impeller is constructed as an equal pressure turbine or action turbine driveable by the dynamic pressure or the kinetic energy of the drive fluid while the static pressure or the enthalpy of the drive fluid is approximately the same upstream and downstream from the first impeller.

29. The handheld element according to claim 26, further comprising a lighting device which is connected to the generator and can be supplied with electric power by the generator.

30. The handheld element according to claim 1, wherein the fluid conducting device is a first fluid conducting device, further comprising a second fluid conducting device for connecting the first fluid conducting device to the generator.

31. The handheld element according to claim 30, wherein the generator is at least partially accommodated in the second fluid conducting device.

32. The handheld element according to claim 1, wherein the generator is surrounded at least partially by an outer shell positioned within the outer sleeve, wherein the outer shell is releasably insertable into the fluid conducting device.

33. The handheld element according to claim 32, wherein the outer shell of the generator is spaced apart inwardly from an inner wall of the fluid conducting device surrounding the outer shell of the generator, so that a fluid channel for conducting the fluid stream is formed between the outer shell of the generator and the inner wall of the fluid conducting device, further comprising a passage connected to the fluid channel for conducting the fluid stream toward and/or away from the second impeller.

34. The handheld element according to claim 33, wherein the passage is defined in the outer shell of the generator, so that the fluid stream can be conducted through the outer shell of the generator.

35. The handheld element according to claim 1, wherein the handheld element is an adaptor or coupling device, and wherein the first impeller is arranged in a handpiece part detachably connectible to the handheld element.

36. The handheld element according to claim 16, wherein the generator is surrounded at least partially by an outer shell which is releasably insertable into the fluid conducting device.

37. The handheld element according to claim 14, wherein the handheld element comprises two parts, wherein each of the two parts of the handheld element comprises one of the first and second impellers and wherein the two parts of the handheld element are able to be releasably connected with each other.

38. The handheld element according to claim 37, wherein the two parts of the handheld element are formed by a first part comprising a handpiece or contra-angle handpiece and by a second part comprising a coupling or an adapter, wherein the generator is arranged in the second part.

39. The handheld element according to claim 38, wherein a lighting device, which is connected electrically with the generator, is provided in the second part.

* * * * *